US006258380B1

(12) United States Patent
Overholt

(10) Patent No.: US 6,258,380 B1
(45) Date of Patent: Jul. 10, 2001

(54) CHEWABLE SOFT CAPSULE

(75) Inventor: Susan M. Overholt, McLeansville, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 0 days.

(21) Appl. No.: 09/262,660

(22) Filed: Mar. 5, 1999

(51) Int. Cl.$^7$ .............................. A61K 9/64; A61K 9/66; A61K 9/48
(52) U.S. Cl. .......................... 424/456; 424/451; 424/455
(58) Field of Search ..................... 424/456, 451, 424/455

(56) References Cited

U.S. PATENT DOCUMENTS

| | | |
|---|---|---|
| 1,061,111 | 5/1913 | Olsson . |
| 2,349,430 | 5/1944 | Hiatt et al. ............................. 167/83 |
| 2,580,683 | 1/1952 | Kreuger ................................. 99/165 |
| 2,851,364 | 9/1958 | Peebles ................................. 99/130 |
| 2,853,421 | 9/1958 | Adams et al. ........................ 167/82 |
| 3,057,723 | 10/1962 | Jeffreys et al. ....................... 96/99 |
| 3,126,321 | 3/1964 | Kurtz ..................................... 167/83 |
| 3,228,789 | 1/1966 | Glassman ............................. 117/118 |
| 3,427,378 | 2/1969 | Henderson et al. ................... 424/14 |
| 3,765,917 | 10/1973 | Hijiya et al. .......................... 106/126 |
| 3,865,603 | 2/1975 | Szymanski et al. .................. 106/130 |
| 4,187,119 | 2/1980 | Battard et al. ........................ 106/126 |
| 4,198,391 | 4/1980 | Grainger ................................. 424/37 |
| 4,428,927 | 1/1984 | Ebert et al. ............................. 424/37 |
| 4,450,179 | 5/1984 | Vink et al. ............................. 426/103 |
| 4,532,126 | 7/1985 | Ebert et al. ............................. 424/48 |
| 4,673,438 | 6/1987 | Wittwer et al. ....................... 106/126 |
| 4,719,112 | 1/1988 | Mayer et al. ......................... 424/456 |
| 4,744,988 | 5/1988 | Brox ...................................... 424/456 |
| 4,804,542 | 2/1989 | Fischer et al. ........................ 424/456 |
| 4,935,243 | * 6/1990 | Borkan et al. ........................ 424/441 |
| 5,780,056 | * 7/1998 | Akamatsu et al. ................... 424/464 |

FOREIGN PATENT DOCUMENTS 610538   11/1948   (GB) .

* cited by examiner

Primary Examiner—Thurman K. Page
Assistant Examiner—Todd D Ware
(74) Attorney, Agent, or Firm—Rhodes & Mason, P.L.L.C.

(57) ABSTRACT

The present invention comprises chewable, soft gelatin capsules having a sheath formed of a mixture of a low bloom and a medium bloom gelatins, a plasticizer, water, and preferably a moisture retention agent to enhance the machinability and integrity of the sheath composition; and a fill of an active material in a carrier liquid.

22 Claims, No Drawings

CHEWABLE SOFT CAPSULE

BACKGROUND OF THE INVENTION (1) Field of the Invention

The present invention relates generally to soft gelatin capsules and to a process for their preparation, and in particular to soft gelatin capsules having a chewable consistency.

(2) Description of the Prior Art

Soft gelatin capsules are comprised of a gelatin sheath encapsulating a fill of a medicament, vitamin, or other material to be consumed by the user. The one-piece gelatin sheath or shell includes a plasticizer, normally glycerin or sorbitol, to control the softness and flexibility of the sheath. The sheath also includes water, and optionally, other additives, such as flavorants. The fill is normally comprised of a carrier in which the active material is dissolved or suspended.

Chewable soft gelatin capsules, or chewable softgels, are designed so that the user chews upon the capsule to release the fill into the mouth instead of swallowing the capsule with the fill still encapsulated within the sheath. Chewable capsules are particularly suitable for administering analgesics, vitamins, minerals and cold remedies. After the fill has been released, the user chews the fractured sheath until it is partially or completely dispersed. In an alternative embodiment described in U.S. Pat. No. 4,428,927, a chewing gum base material is incorporated into the sheath and the sheath is not made for swallowing.

Therefore, acceptable sheath formulations must not only have sufficient integrity to encapsulate the fill without leakage prior to consumption, they must also be readily soluble or dispersible when chewed. In addition, the formulations must not be of a sticky or tacky nature during processing, interfering with the conversion of the gelatin mass into sheaths in conventional encapsulation equipment.

While an effective delivery system, the acceptance of chewable softgels has been limited by the mouth-feel or texture of the sheath, which is commonly perceived to be leathery or rubbery, and the difficulty in consuming the fractured sheaths after the fill has been released. The use of chewable softgels could be significantly expanded if this problem could be overcome.

SUMMARY OF THE INVENTION

The present invention is directed to chewable soft gelatin capsules, or chewable softgels comprised of a chewable gelatin sheath encapsulating a liquid fill. The sheath composition is specifically characterized by flexibility and a non-sticky consistency so that it can be formed into capsules using conventional encapsulation machinery, and the integrity to enclose a fill for an extended period of time, e.g., up to about two years, without dissolution or leakage, while still being readily soluble upon consumption.

Most conventional softgel capsules are produced by a rotary die process in which a molten mass of a gelatin sheath formulation is fed from a reservoir onto drums to form two spaced sheets or ribbons of gelatin in a semi-molten state. These ribbons are fed around rollers and brought together at a convergent angle into the nip of a pair of roller dies that include opposed die cavities. A liquid or paste medicament or other material to be encapsulated is fed into the wedge-shaped joiner of the ribbons.

The gelatin ribbons are continuously conveyed between the dies, with portions of the medicament being trapped between the sheets inside the die cavities. The sheets are then pressed together, and severed around each die so that opposed edges of the sheets flow together to form a continuous gelatin sheath around the entrapped medicament. The part of the gelatin sheet that is severed from the segments forming the capsules is then collected for recycling. The very soft capsules are then dried to increase the integrity of the sheath, and packaged for later distribution and consumption.

Manufacture of uniform soft gelatin capsules by this or similar processes requires a sheath material that has good "machineability," i.e., it is of critical importance that the sheath material be of a non-tacky or non-sticky nature, so that the sheath material can be brought into contact with the rollers without sticking. At the same time, the sheath composition must not degrade or dissolve during storage prior to consumption, allowing the fill material to leak from the capsule.

The properties of the sheath material is determined in significant part by the cohesive strength of the constituent gelatin, expressed as "bloom." Conventional soft gelatin capsules normally have a bloom in the range of from about 150 to about 275. This bloom value is determined by measuring the weight in grams required to move a plunger 0.5 inch in diameter, 4 mm into a 6.67% gelatin gel that has been held for 17 hours at 10° C.

Chewable softgel capsule sheaths are designed to at least partially disperse or dissolve in the user's mouth within a brief period of time after the fill contents have been released, e.g., within about 60 seconds, so that it can be swallowed. Therefore, in addition to the above properties, the sheath of these products must also be soluble after the fill contents are released. The sheath should also have a good "mouth feel." As used herein, "mouth feel" describes chewability. Chewing the sheath should be a pleasant, or at least not an unpleasant sensation that results in a swallowable composition.

Surprisingly, it has been found that a chewable softgel sheath having all of these desired characteristics can be produced from a specific mixture of defined gelatins in combination with defined percentages of a plasticizer and preferably a moisture retaining agent. This combination of ingredients, to be described herein in detail, has been found to produce capsule sheaths that have the necessary low stickiness for machineability, and sufficient integrity for stable fill encapsulation, while having a desirable mouth-feel and solubility.

More specifically, the present capsule sheaths are formed of a mixture of a first gelatin having a bloom substantially lower than the bloom of gelatins conventionally used to form capsule sheaths, in combination with a minor percentage of a second gelatin having a bloom within the range of conventional sheath-forming gelatin blooms. The first gelatin has insufficient integrity for use alone in sheath formation.

Plasticizers are essential in sheath formulations in order to impart the necessary softness and flexibility to the sheath material, so it can be formed into capsules. The presence of a significant percentage of plasticizer, however, may result in a sheath that is difficult to process because the sheath will stick to the rollers during machining, as described herein above. Also, the plasticizers tend to dry out the sheath over any extended shelf-life of the finished product capsule, resulting in a capsule with a "leathery" mouth feel.

In accordance with an additional embodiment of the present invention, the tackiness or stickiness of the sheath can be maintained at a desired machinable level, even in the presence of high percentages of plasticizers, by adding a small percentage of a moisture retention agent, as hereafter defined, to the sheath composition. The moisture retention agent also maintains the desired mouth feel over an extended shelf-life.

While the function of the moisture retention agent is not entirely clear, it appears that the additive disrupts the gelatin structure to reduce the gelatin strength and immobilizes or retains water.

More specifically, the present sheath composition is comprised of a first gelatin, hereinafter referred to as "low bloom" gelatin, having a bloom of up to about 100, and preferably from about 80 to about 100. The low bloom gelatin is combined with a second gelatin, hereinafter referred to as "medium bloom" gelatin, having a bloom in the range of from about 150 to about 275, and preferably from about 150 to about 175. The first and second gelatins preferably are present in a ratio of from about 1:1 to about 10:1, and even more preferably a ratio of from about 3:1 to about 5:1. Type A or B gelatins or a mixture thereof, may be used for the first and/or the second gelatin. Limed bone, acid bone, fish and/or pig skin gelatins may be used in the present invention.

The sheath plasticizer preferably is glycerin, sorbitol, maltitol, or a mixture thereof. Other plasticizing agents known in the art to improve softness and flexibility are also within the scope of the present invention. The sheath will normally include at least about 10 percent by weight plasticizer in order to impart the desired softness and flexibility. Preferably, from about 20 to about 30 percent by weight of plasticizer will be employed.

As noted earlier, when the required percentages of plasticizer are combined with the above-described gelatin mixture, the capsule may not have desired machinability or extended chewability characteristics. However, it has been found these characteristics are improved by adding at least about 0.5% by weight, and preferably from about 1 to about 5% by weight of a moisture retention agent to the composition.

Materials used in the present invention as moisture retention agents have been previously added to sheaths used to encapsulate water miscible, volatile fills, see, e.g., U.S. Pat. No. 4,804,542. In these prior art compositions, the materials are used to prevent dissolution of the sheath by the particular fills used. In the present invention, however, the moisture retention agent serves a different purpose, namely, to improve machinability and prevent the sheath of the finished capsule from drying out. In addition, the moisture retention material finds use in both water miscible, volatile fills, and with carriers of the type described below, where such materials have not previously been used or required.

Although not meant to limit the scope of the present invention, examples of moisture retaining agents include celluloses, cellulose derivatives, starches, starch derivatives, vegetable gums, non-hygroscopic, mono-, di- and oligosaccharides, and silicon dioxide. Specific stabilizers are: starches such as LO-TEMP®, SOFT-SET®, OR MIRA-GEL® manufactured by A.E. Staley Manufacturing Company of Decatur, Ill.; microcrystalline cellulose such as AVICEL® manufactured by FMC corporation of Philadelphia, Pa.; silicon dioxide such as AEROSIL® manufactured by Degussa Aktiengesellschaft of Frankfurt, Germany; and cellulose such as SOLKA FLOC® manufactured by Fiber Sales & Development Corporation of Urbana, Ohio.

Other sheath ingredients may include taste modifiers. For example, non-reducing sugars, such as xylitol, maltitol, or LYCASIN® manufactured by Roquette America, Inc. of Keokuk, Iowa, are commonly added to the composition. These non-reducing sugars are usually added in amounts up to about 10% of the sheath composition.

Thus, the preferred sheath compositions of the present invention are comprised of the following ingredients in the specified percentages:

| INGREDIENT | % BY WEIGHT |
|---|---|
| Low Bloom Gelatin | 15–30 |
| Medium Bloom Gelatin | 5–15 |
| Plasticizer | 20–40 |
| Water | 10–30 |
| Moisture Retaining Agent | 0.5–5 |
| Other Ingredients | 0–10 |

It will be understood that different percentages may be selected within the above ranges so that the sum of the percentages of the sheath ingredients is equal to 100%. If additional ingredients are used, the percentages will be adjusted within the ranges listed to accommodate the additional ingredients.

Based upon the preferred composition described immediately hereinabove, upon casting the sheath into gelatin capsules it is known in the art that the drying process will reduce the water content of the sheath to less than about 10%, with a preferred industry standard of about 6% to about 8%. Accordingly, the capsule sheath formed from the above mixture, after being dried for storage and subsequent use, preferably is comprised of the following ingredients in the specified parts by weight:

| INGREDIENT | PARTS BY WEIGHT |
|---|---|
| Low Bloom Gelatin | 20–38 |
| Medium Bloom Gelatin | 6–20 |
| Plasticizer | 26–52 |
| Water | 6–8 |
| Moisture Retaining Agent | 0.60–6.50 |
| Other Ingredients | 0–13 |

The capsule fill is generally comprised of a liquid carrier, and an active ingredient dissolved or suspended therein. The liquid carrier preferably is a water-immiscible liquid such as a vegetable and aromatic oils, aromatic and aliphatic and aliphatic hydrocarbons, chlorinated hydrocarbons, ethers, esters, high molecular weight organic acids and alcohols, or lower molecular weight polyalkylene glycols, such as polyalkylene glycol 600. Other embodiments may contain water-miscible liquid carriers as well.

As used in the present description, the term "active ingredient" is intended to include medicaments, vitamins, minerals, fruits, herbals and other encapsulatable materials or combinations thereof understood by those skilled in the art to support the desired effect. For example, if the effect desired is mineral supplementation, exemplary active ingredients may be calcium, magnesium and Vitamin D. Additionally, if the desired effect is targeted toward urinary tract health, an exemplary active ingredient of cranberry is included.

The fill may also include other ingredients, such as sweeteners and other flavorants, or flavor modifiers. Suitable flavor modifiers include any natural or artificial flavor or a combination thereof. Also, as is known in the industry, WONF (with other natural flavors) flavorants may be included.

Generally, the active ingredient will be present in an amount of from up to about 50% by weight, with variations allowed for the variable fill employed. Mixtures of active ingredients may also be incorporated into the fill.

EXAMPLES

The following examples describe the manufacture and testing of various sheath formulations for acceptable chewability, and for low tack or stickiness. Chewability is a subjective test in which chewability is evaluated by considering such factors as the mouth feel of the capsule, and the ease of dissolution or dispersion in the mouth and the ease of swallowing the fractured sheath.

The tendency of the sheath to stick to rollers is estimated with the use of a texture analyzer in which the force (g) required to remove the gelatin sheath from a simulated casting machine is measured. As a base line requirement for the preferred embodiment of the present invention, a value of 35 g or less was established based upon testing conventional gelatin sheath compositions. The preferred texture is variable depending upon the specific manufacturing process employed. As discussed above, most softgels are manufactured through a rotary die process, however, the present invention should not be limited thereto. Other appropriate manufacturing processes are also within the scope of this invention.

As will be seen from the Examples, the chewability and machineability of a given sheath formulation is dependent upon the combination of gelatins used, the amount of plasticizer, and the presence and amount of a moisture retention agent. The optimum percentages of each ingredient will depend upon the overall formulation contents, and the identity of the individual ingredients. However, evaluation and selection of the most desirable formulation will be well within the skill of practitioners in this area, once they are familiar with the present disclosure.

For Tables 1 and 2, the following abbreviations are used: S—S for SOFT-SET®; L-T for LO-TEMP®; Sorb for Sorbitol; Aero for AEROSIL®; Avi for AVICEL®; and S-F for SOLKA FLOC®, each component being described more fully above.

TABLE 1

| | Experiments 1–10 | | | | | | | | | |
|---|---|---|---|---|---|---|---|---|---|---|
| COMPONENT | 1 | 2 | 3 | 4 | 5 | 6 | 7 | 8 | 9 | 10 |
| 100 Bloom | 31.7 | 30.6 | 23.1 | 23.1 | 23.13 | 23.54 | 23.54 | 24.13 | 23.54 | 26.54 |
| 150 Bloom | | 5.1 | 12.5 | 12.5 | 12.54 | 10 | 6 | 6 | 10 | 6 |
| 275 Bloom | | | | | | | | | | |
| Glycerin | 24 | 24 | 29.9 | 29.9 | 29.9 | 29.9 | 29.9 | 29.9 | 26.9 | 26.9 |
| Water | 15.1 | 18.7 | 25.7 | 25.7 | 25.7 | 25.4 | 29.9 | 25.77 | 25.77 | 25.77 |
| Lycasin ® - 75% Solids | | 20.7 | 6.5 | 6.5 | 3.28 | 3.28 | 3.28 | 6.28 | 3.28 | 5.83 |
| Xylitol | | | | | | 4.83 | 3.28 | 5.28 | 3.28 | 3.28 |
| Crystalliized Fructose | | 2.9 | | | 3.28 | | | | | |
| Starch | | | 2 S-S | 2 L-T | | 3 L-T | 3 L-T | 2 L-T | 3 L-T | 3 L-T |
| Cellulose | | | | | | | | | | |
| Other | | | | | 2 Pectin | | 5.54 Sorb | 0.55 Aero | 4.13 Sorb | 4.13 Sorb |
| Texture Analyzer (g) | 1050 | 800 | 28.5 | 25.5 | 19.7 | 19 | 20 | 21 | 23.5 | 15.1 |

| TABLE 1a | COMMENTS |
|---|---|
| Exp. 1 | Very tacky and sticky |
| Exp. 2 | Very tacky and sticky |
| Exp. 3 | Added additional water; Performance OK |
| Exp. 4 | Texture and chewability acceptable |
| Exp. 5 | Too much self tack |
| Exp. 6 | Excellent texture and chewability characteristics |
| Exp. 7 | Chewability was great, but very self-tacky |
| Exp. 8 | Gel was acceptable |
| Exp. 9 | Performance was good, but tough with time |
| Exp. 10 | Excellent gel texture and chewability |

TABLE 2

| | Experiments 11–20 | | | | | | | | | |
|---|---|---|---|---|---|---|---|---|---|---|
| COMPONENT | 11 | 12 | 13 | 14 | 15 | 16 | 17 | 18 | 19 | 20 |
| 100 Bloom | 23.13 | 23.12 | 26.54 | 24 | 24 | 23 | 23 | 23 | 25 | 25 |
| 150 Bloom | 12 | 12 | 6 | 6 | 12 | 12 | 8 | 6 | | |

TABLE 2-continued

| Experiments 11–20 | | | | | | | | | | |
|---|---|---|---|---|---|---|---|---|---|---|
| 275 Bloom | | | | | | | | | 5 | 5 |
| Glycerin | 26 | 26 | 26.9 | 27 | 26 | 26 | 26 | 26 | 30 | 28.5 |
| Water | 25.77 | 25.77 | 25.77 | 26 | 25.77 | 26 | 29 | 30 | 30 | 30 |
| Lycasin ® - 75% Solids | 7.27 | 3.28 | 5.28 | 7.3 | 7 | 7 | 7 | 7 | 4 | 4 |
| Xylitol Crystallized Fructose | 3.38 | 3.28 | 3.28 | 6.3 | 3 | 5 | 5 | 5 | 4 | 4 |
| Starch | 2 L-T | 2 L-T | 3 L-T | 2 L-T | 2 L-T | | | | | |
| Cellulose | | | | | | 1 S-F | 2 Avi | 3 Avi | 2 S-F | 3.5 Avi |
| Other | .544 Aero | 3.98 Sorb | 4.13 Sorb | 1 Sorb | 2.26 Aero | | | | | |
| Texture Analyzer (g) | 19 | 18 | 14.9 | 15 | 13 | 38 | 15 | 11 | 19 | 25 |

| Table 2a | COMMENTS |
|---|---|
| Exp. 11 | Gel was very tough initially |
| Exp. 12 | Acceptable performance |
| Exp. 13 | Excellent chewability, self-tack may be a problem |
| Exp. 14 | Acceptable performance |
| Exp. 15 | Acceptable performance |
| Exp. 16 | Too sticky |
| Exp. 17 | Excellent texture analyzer and chewability characteristics |
| Exp. 18 | Excellent texture analyzer and chewability characteristics |
| Exp. 19 | Excellent texture analyzer and chewability characteristics |
| Exp. 20 | Acceptable texture and chewability characteristics |

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A gelatin capsule sheath comprised of:
   a) from about 20 to about 38% by weight of a first gelatin having a bloom of from about 80 to about 100;
   to b) from about 6 to about 20% by weight of a second gelatin having a bloom of from about 150 to about 275;
   c) up to about 10% water;
   c) a plasticizer in an amount sufficient to render said sheath flexible; and
   d) a moisture retention agent in an amount sufficient to provide sheath integrity.

2. The sheath of claim 1, wherein said plasticizer is selected from the group consisting of glycerin, sorbitol, maltitol, and mixtures thereof.

3. The sheath of claim 1, wherein said plasticizer is present in an amount of from about 26 to about 52% by weight of said sheath.

4. The sheath of claim 1, wherein said moisture retention agent is selected from the group consisting of celluloses, cellulose derivatives, starches, starch derivatives, vegetable gums, non-hygroscopic, mono-, di- and oligo-saccharides, and silicon dioxide.

5. The sheath of claim 1, wherein said moisture retention agent is present in an amount of from about 0.6 to about 6.5% by weight of said sheath.

6. A chewable, gelatin capsule with a continuous soft sheath encapsulating a fill, said sheath including
   a) from about 20 to about 38 parts by weight of a first gelatin having a bloom of from about 80 to about 100;
   b) from about 6 to about 20 parts by weight of a second gelatin having a bloom of from about 150 to about 275;
   c) from about 6 to about 8 parts by weight of water;
   c) a plasticizer in an amount sufficient to render said sheath flexible; and
   d) a moisture retention agent in an amount sufficient to provide sheath integrity.

7. The capsule of claim 6, wherein said fill is comprised of a carrier liquid and an active material.

8. The capsule of claim 7, wherein said carrier liquid is a water-immiscible liquid selected from the group consisting of vegetable oils, aromatic oils, aromatic and aliphatic hydrocarbons, chlorinated hydrocarbons, ethers, esters, high molecular weight organic acids, alcohols, and lower molecular weight polyalkylene glycols.

9. The capsule of claim 7, wherein said moisture retention agent is selected from the group consisting of celluloses, cellulose derivatives, starches, starch derivatives, vegetable gums, non-hygroscopic, mono-, di- and oligo-saccharides, and silicon dioxide.

10. The capsule of claim 7, wherein said active material is selected from the group consisting of medicaments, vitamins, minerals, fruits, and herbals.

11. A method for forming a chewable gelatin sheath comprising:
   a) providing a mixture of about 15 to about 30% by weight of a first gelatin having a bloom of from about 80 to about 100, from about 5 to about 15% by weight of a second gelatin having a bloom of from about 150 to about 275, from about 10 to about 30 water, and an amount of a plasticizer sufficient to render said sheath flexible; and
   b) forming a film from said mixture.

12. The method of claim 11, wherein said mixture further includes a moisture retention agent in an amount sufficient to provide sheath integrity.

13. The method of claim 11, wherein said plasticizer is selected from the group consisting of glycerin, sorbitol, maltitol, and mixtures thereof.

14. The method of claim 11, wherein said plasticizer is present in an amount of from about 20 to about 40% by weight of said mixture.

15. The method of claim 11, wherein said moisture retention agent is selected from the group consisting of celluloses, cellulose derivatives, starches, starch derivatives, vegetable gums, non-hygroscopic, mono-, di- and oligo-saccharides, and silicon dioxide.

16. The method of claim 12, wherein said moisture retention agent is present in an amount of from about 0.5 to about 5% by weight of said sheath.

17. A method for manufacturing chewable soft gelatin capsules comprising:
   a) providing a mixture of about 15 to about 30% by weight of a first gelatin having a bloom of from about 80 to about 100, from about 5 to about 15% by weight of a second gelatin having a bloom of from about 150 to about 275, from about 10 to about 30 water, and an amount of a plasticizer sufficient to render said mixture flexible; and
   b) encapsulating a film from said mixture.

18. The method of claim 17, wherein said mixture further includes a moisture retention agent in an amount sufficient to provide sheath integrity.

19. The method of claim 17, wherein said fill includes a carrier liquid selected from the group consisting of vegetable oils, aromatic oils, aromatic and aliphatic hydrocarbons, chlorinated hydrocarbons, ethers, esters, high molecular weight organic acids, alcohols, and lower molecular weight polyalkylene glycols.

20. The method of claim 17, wherein said plasticizer is selected from the group consisting of glycerin, sorbitol, maltitol, and mixtures thereof.

21. The method of claim 17, wherein said moisture retention agent is selected from the group consisting of celluloses, cellulose derivatives, starches, starch derivatives, vegetable gums, non-hygroscopic, mono-, di- and oligo-saccharides, and silicon dioxide.

22. The method of claim 17, wherein said active material is selected from the group consisting of medicaments, vitamins, minerals, fruits, and herbals.

* * * * *

UNITED STATES PATENT AND TRADEMARK OFFICE
CERTIFICATE OF CORRECTION

PATENT NO. : 6,258,380 B1  
DATED : July 10, 2001  
INVENTOR(S) : Susan M. Overholt, Ph.D.

Page 1 of 1

It is certified that error appears in the above-identified patent and that said Letters Patent is hereby corrected as shown below:

Title page,
Inventor's name should read: -- Susan M. Overholt, Ph.D. --

Claim 17,
Line 18, should read: -- b) encapsulating a film with said mixture. --

Signed and Sealed this

Nineteenth Day of February, 2002

Attest:

JAMES E. ROGAN
Attesting Officer    Director of the United States Patent and Trademark Office